United States Patent
Busacca et al.

(10) Patent No.: US 7,544,798 B2
(45) Date of Patent: Jun. 9, 2009

(54) PROCESS FOR PREPARING MACROCYCLIC COMPOUNDS

(75) Inventors: Carl Alan Busacca, Poughkeepsie, NY (US); Vittorio Farina, Ridgefield, CT (US); Fabrice Gallou, Basel (CH); Nizar Haddad, Danbury, CT (US); Xiao-jun Wang, Danbury, CT (US); Xudong Wei, Ridgefield, CT (US); Jinghua Xu, Bethel, CT (US); Yibo Xu, New Milford, CT (US); Nathan K. Yee, Danbury, CT (US); Li Zhang, New Milford, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/670,140

(22) Filed: Feb. 1, 2007

(65) Prior Publication Data

US 2008/0177029 A1    Jul. 24, 2008

Related U.S. Application Data

(63) Continuation of application No. 11/078,074, filed on Mar. 11, 2005, now abandoned.

(60) Provisional application No. 60/553,317, filed on Mar. 15, 2004, provisional application No. 60/578,123, filed on Jun. 8, 2004.

(51) Int. Cl.
C07K 5/08    (2006.01)
C07D 215/16    (2006.01)

(52) U.S. Cl. ...................... 540/460; 546/153

(58) Field of Classification Search ............. 540/460; 546/153
See application file for complete search history.

(56) References Cited

U.S. PATENT DOCUMENTS

| | | | |
|---|---|---|---|
| 6,323,180 B1 | 11/2001 | Llinas-Brunet et al. | |
| 6,608,027 B1 | 8/2003 | Tsantrizos et al. | |
| 6,867,185 B2 | 3/2005 | Campbell et al. | |
| 2003/0224977 A1 | 12/2003 | Llinas-Brunet et al. | |
| 2004/0248779 A1 | 12/2004 | Dersch et al. | |
| 2005/0080005 A1 | 4/2005 | Llinas-Brunet et al. | |
| 2005/0267151 A1 | 12/2005 | Busacca et al. | |

FOREIGN PATENT DOCUMENTS

| WO | 0009543 | 2/2000 |
|---|---|---|
| WO | 0009558 | 2/2000 |
| WO | 03053349 A2 | 7/2003 |
| WO | 03099274 A1 | 12/2003 |
| WO | 2004037855 A1 | 5/2004 |
| WO | 2004092203 A2 | 10/2004 |

*Primary Examiner*—Bruck Kifle
(74) *Attorney, Agent, or Firm*—Michael P. Morris; Mary-Ellen M. Devlin; Philip I. Datlow

(57) ABSTRACT

Disclosed is a multi-step process for preparing a macrocyclic compound of the formula (I):

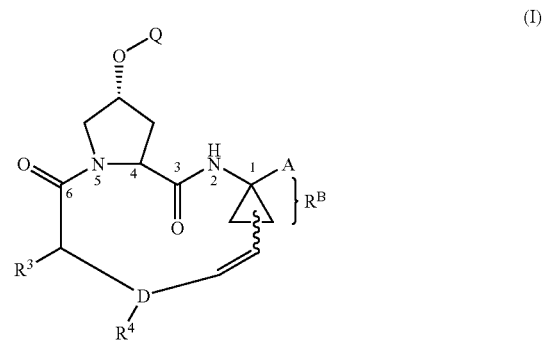

wherein Q is a radical of the following formula:

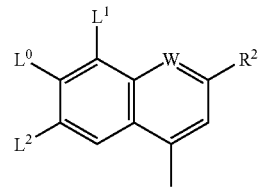

and the other variables are as defined herein. The compounds of formula (I) are potent active agents for the treatment of hepatitis C virus (HCV) infection.

13 Claims, No Drawings

PROCESS FOR PREPARING MACROCYCLIC COMPOUNDS

RELATED APPLICATIONS

This is a continuation of U.S. application Ser. No. 11/078,074 filed on Mar. 11, 2005, which claims, as does the present application, priority benefit of U.S. Provisional Applications 60/553,317, filed Mar. 15, 2004, and 60/578,123, filed Jun. 8, 2004, and which are incorporated herein in their entirety.

BACKGROUND OF THE INVENTION

1. Technical Field

The invention relates to an improved process for the preparation of macrocyclic compounds useful as agents for the treatment of hepatitis C viral (HCV) infections.

2. Background Information

The macrocyclic compounds of the following formula (I) and methods for their preparation are known from: Tsantrizos et al., U.S. Pat. No. 6,608,027 B1; Llinas Brunet et al, U.S. Application Publication No. 2003/0224977 A1; Llinas Brunet et al, WO 2004/037855 Llinas Brunet et al, U.S. application Ser. No. 10/945,518, filed Sep. 20, 2004; Brandenburg et al., WO 2004/092203 and Samstag et al., U.S. Application Publication No. 2004/0248779 A1:

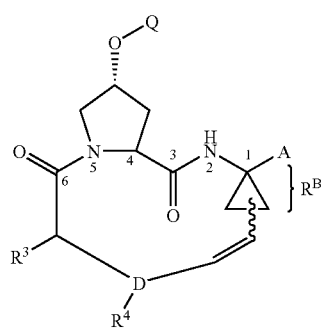

(I)

wherein Q is a substituent of the following formula:

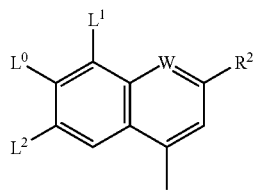

and the other variables are as defined herein.

The compounds of formula (I) are disclosed in the above-mentioned patent documents as being active agents for the treatment of hepatitis C virus (HCV) infections. The methods disclosed for the preparation of these compounds include many synthetic steps, which may involve protection and deprotection of certain reactive groups. The problem addressed by the present invention is to provide a process which allows for the manufacture of these compounds with a minimum number of steps on a technical scale with sufficient overall yield.

BRIEF SUMMARY OF THE INVENTION

Surprisingly, it has been found that a key ring closing metathesis "RCM" reaction step can be carried out successfully in the presence of the quinolone "Q" substituent that potentially could have interfered with the catalyst activity by serving as a ligand. Based on this discovery, it has been found that the compounds of formula (I) described above can be prepared using fewer synthetic steps if the synthesis is carried out using the following general sequence of steps as described herein:

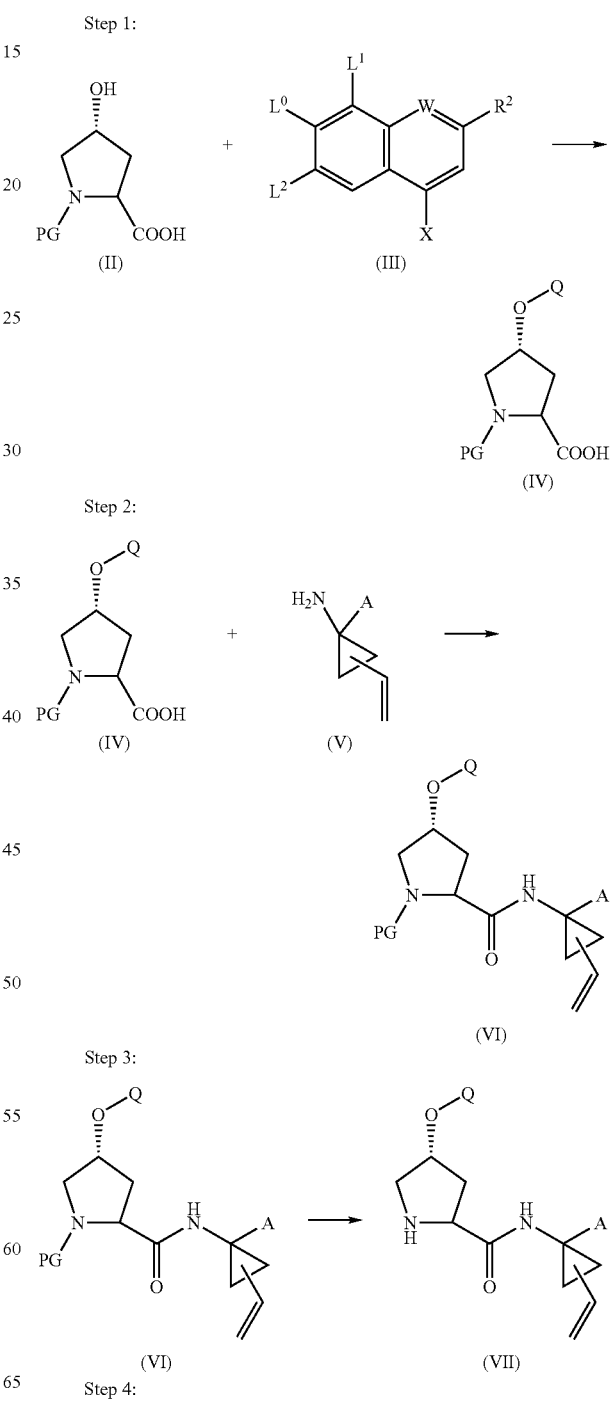

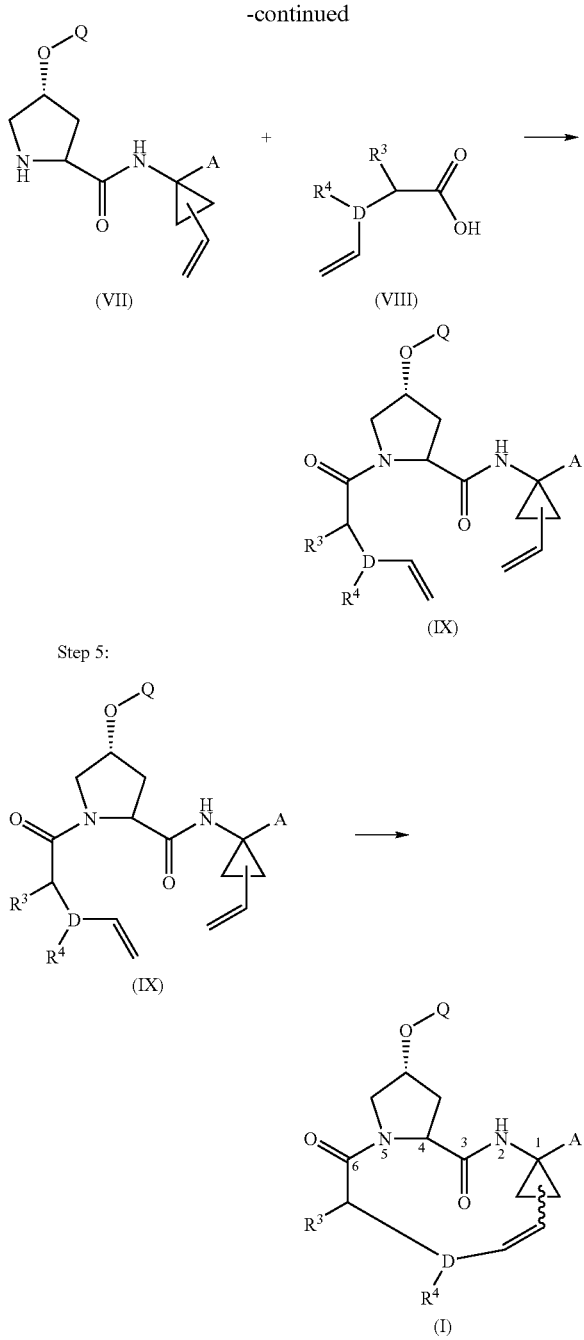

Step 5:

and when A is a protected carboxylic acid group, optionally subjecting the compound of formula (I) to de-protection conditions to obtain a compound of formula (I) wherein A is a carboxylic acid group;

and when A is a carboxylic acid group in the resulting compound of formula (I), optionally coupling this compound with a sulfonamide of formula $R^{114}SO_2NH_2$ in the presence of a suitable coupling agent, such as carbodiimide reagents, TBTU or HATU, to obtain a compound of formula (I) wherein A is —C(O)—NH—$SO_2R^{114}$.

The present invention is therefore directed to a multi-step synthetic process for preparing compounds of formula (I) using the synthetic sequence as described herein; particular individual steps of this multi-step process; and particular individual intermediates used in this multi-step process.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

The term "$C_{1-6}$ alkyl" as used herein, either alone or in combination with another substituent, means acyclic, straight or branched chain alkyl substituents containing from 1 to six carbon atoms and includes, for example, methyl, ethyl, propyl, butyl, hexyl, 1-methylethyl, 1-methylpropyl, 2-methylpropyl, and 1,1-dimethylethyl.

The term "$C_{3-6}$ cycloalkyl" as used herein, either alone or in combination with another substituent, means a cycloalkyl substituent containing from three to six carbon atoms and includes cyclopropyl, cyclobutyl, cyclopentyl, and cyclohexyl.

The term "saturated alkylene chain" as used herein means a divalent alkyl substituent derived by the removal of one hydrogen atom from each end of a saturated straight or branched chain aliphatic hydrocarbon and includes, for example, —$CH_2CH_2C(CH_3)_2CH_2CH_2$—.

The term "$C_{1-6}$ alkoxy" as used herein, either alone or in combination with another substituent, means the substituent $C_{1-6}$ alkyl-O— wherein alkyl is as defined above containing up to six carbon atoms. Alkoxy includes methoxy, ethoxy, propoxy, 1-methylethoxy, butoxy and 1,1-dimethylethoxy. The latter substituent is known commonly as tert-butoxy.

The term "$C_{3-6}$ cycloalkoxy" as used herein, either alone or in combination with another substituent, means the substituent $C_{3-6}$ cycloalkyl-O— containing from 3 to 6 carbon atoms.

The term "$C_{2-7}$ alkoxy-$C_{1-6}$alkyl" as used herein, means the substituent $C_{2-7}$ alkyl-O—$C_{1-6}$ alkyl wherein alkyl is as defined above containing up to six carbon atoms.

The term "halo" as used herein means a halogen substituent selected from bromo, chloro, fluoro or iodo.

The term "haloalkyl" as used herein means as used herein, either alone or in combination with another substituent, means acyclic, straight or branched chain alkyl substituents having one or more hydrogens substituted for a halogen selected from bromo, chloro, fluoro or iodo.

The term "thioalkyl" as used herein means as used herein, either alone or in combination with another substituent, means acyclic, straight or branched chain alkyl substituents containing a thiol (HS) group as a substituent. An example of a thioalkyl group is a thiopropyl, e.g., HS—$CH_2CH_2CH_2$— is one example of a thiopropyl group.

The term "$C_6$ or $C_{10}$ aryl" as used herein, either alone or in combination with another substituent, means either an aromatic monocyclic system containing 6 carbon atoms or an aromatic bicyclic system containing 10 carbon atoms. For example, aryl includes a phenyl or a naphthyl ring system.

The term "$C_{7-16}$ aralkyl" as used herein, either alone or in combination with another substituent, means an aryl as defined above linked through an alkyl group, wherein alkyl is as defined above containing from 1 to 6 carbon atoms. Aralkyl includes for example benzyl, and butylphenyl.

The term "Het" as used herein, either alone or in combination with another substituent, means a monovalent substituent derived by removal of a hydrogen from a five-, six-, or seven-membered saturated or unsaturated (including aromatic) heterocycle containing carbon atoms and from one to four ring heteroatoms selected from nitrogen, oxygen and sulfur. Examples of suitable heterocycles include: tetrahydrofuran, thiophene, diazepine, isoxazole, piperidine, dioxane, morpholine, pyrimidine or

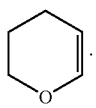

The term "Het" also includes a heterocycle as defined above fused to one or more other cycle be it a heterocycle or a carbocycle, each of which may be saturated or unsaturated. One such example includes thiazolo[4,5-b]-pyridine. Although generally covered under the term "Het", the term "heteroaryl" as used herein precisely defines an unsaturated heterocycle for which the double bonds form an aromatic system. Suitable example of heteroaromatic system include: quinoline, indole, pyridine,

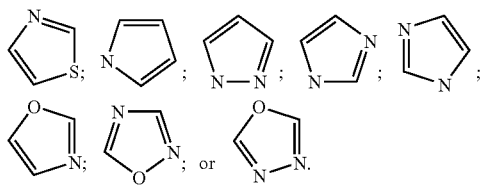

The term "oxo" means the double-bonded group (=O) attached as a substituent.

The term "thio" means the double-bonded group (=S) attached as a substituent.

In general, all tautomeric forms and isomeric forms and mixtures, whether individual geometric isomers or optical isomers or racemic or non-racemic mixtures of isomers, of a chemical structure or compound are intended, unless the specific stereochemistry or isomeric form is specifically indicated in the compound name or structure.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

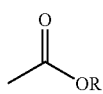

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters are found in *Design of Prodrugs*, Bundgaard, H. Ed. Elsevier (1985) incorporated herewith by reference. Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" as used herein includes those derived from pharmaceutically acceptable bases. Examples of suitable bases include choline, ethanolamine and ethylenediamine. $Na^+$, $K^+$, and $Ca^{++}$ salts are also contemplated to be within the scope of the invention (also see *Pharmaceutical Salts*, Birge, S. M. et al., J. Pharm. Sci., (1977), 66, 1-19, incorporated herein by reference).

The following chemicals may be referred to by these abbreviations:

| Abbreviation | Chemical Name |
| --- | --- |
| ACN | Acetonitrile |
| Boc | Tert-butoxylcarbonyl |
| DABCO | 1,4-diazabicyclo[2.2.2]octane |
| DBU | 1,8-Diazabicyclo[5.4.0]undec-7-ene |
| DCC | 1,3-Dicyclohexylcarbodiimide |
| DCHA | Dicyclohexylamine |
| DCM | Dichloromethane |
| DIPEA | Diisopropylethylamine or Hünigs-Base |
| DMAP | Dimethylaminopyridine |
| DMF | N,N-Dimethylformamide |
| DMSO | Dimethylsulfoxide |
| DMTMM | 4-(4,6-Dimethoxy-1,3,5-triazin-2-yl)-4-methylmorpholinium Chloride |
| EDC | 1-(3-dimethylaminopropyl)-3-ethylcarbodiinide hydrocholide |
| HATU | O-(7-azabenzotriazol-1-yl)-N,N,',N'-tetramethyluronium hexafluorophosphate |
| HBTU | O-Benzotriazol-1-yl-N,N,',N'-tetramethyluronium hexafluorophosphate |
| HOAT | 1-Hydroxy-7-azabenzotriazole |
| HOBT | 1-Hydroxybenzotriazole |
| IPA | Isopropyl alcohol |
| KDMO | Potassium 3,7-dimethyl-3-octanoxide |
| MCH | Methylcyclohexane |
| MIBK | 4-Methyl-2-pentanone |
| NMP | 1-Methyl-2-pyrrolidinone |
| SEH | Sodium 2-ethylhexanoate |
| TBTU | O-(Benzotriazol-1-yl)-N,N,N',N'-tetramethyluronium tetrafluoroborate |
| THF | Tetrahydofuran |
| THP | Trishydroxymethylphosphine |
| TKC | Tetrakis hydroxymethyl phosphonium chloride |

EMBODIMENTS OF THE INVENTION

In the synthetic schemes below, unless specified otherwise, all the substituent groups in the chemical formulas shall have the same meanings as in the Formula (I). The reactants used in the synthetic schemes described below may be obtained either as described herein, or if not described herein, are themselves either commercially available or may be prepared from commercially available materials by methods known in the art. Certain starting materials, for example, may be obtained by methods described in the International Patent Applications WO 00/59929, WO 00/09543 and WO 00/09558, U.S. Pat. No. 6,323,180 B1 and U.S. Pat. No. 6,608,027 B1.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

I. General Multi-Step Synthetic Method

In one embodiment, the present invention is directed to a general multi-step synthetic method for preparing the compounds of formula (I). Specifically, this embodiment is directed to a process for preparing a compound of the following formula (I):

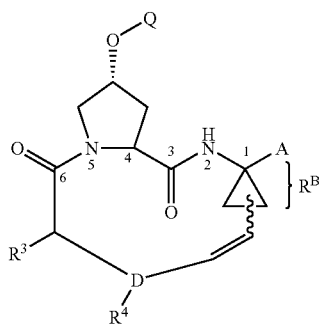

wherein Q is a substituent of the following formula:

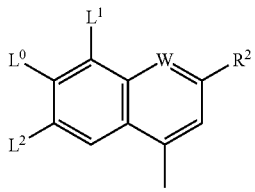

wherein W is CH or N, $L^0$ is H, halo, $C_{1-6}$ alkyl, $C_{3-6}$ cycloalkyl, $C_{1-6}$ haloalkyl, $C_{1-6}$ alkoxy, $C_{3-6}$ cycloalkoxy, hydroxy, or $N(R^{23})_2$, wherein each $R^{23}$ is independently H, $C_{1-6}$ alkyl or $C_{3-6}$ cycloalkyl;

$L^1$, $L^2$ are each independently H, halogen, $C_{1-4}$alkyl, —O—$C_{1-4}$alkyl, or —S—$C_{1-4}$alkyl (the sulfur being in any oxidized state); or $L^0$ and $L^1$ or $L^0$ and $L^2$ may be covalently bonded to form together with the two C-atoms to which they are linked a 4-, 5- or 6-membered carbocyclic ring wherein one or two (in the case of a 5- or 6-membered ring) —CH$_2$— groups not being directly bonded to each other, may be replaced each independently by —O— or NR$^a$ wherein R$^a$ is H or $C_{1-4}$alkyl, and wherein said ring is optionally mono- or di-substituted with $C_{1-4}$ alkyl;

$R^2$ is H, halo, $C_{1-6}$ alkyl, $C_{3-6}$ cycloalkyl, $C_{1-6}$ haloalkyl, $C_{1-6}$ thioalkyl, $C_{1-6}$ alkoxy, $C_{3-6}$ cycloalkoxy, $C_{2-7}$ alkoxy-$C_{1-6}$ alkyl, $C_{6\,or}\,C_{10}$ aryl or Het, wherein Het is a five-, six-, or seven-membered saturated or unsaturated heterocycle containing from one to four heteroatoms selected from nitrogen, oxygen and sulfur;

said cycloalkyl, aryl or Het being substituted with $R^6$, wherein $R^6$ is H, halo, $C_{1-6}$ alkyl, $C_{3-6}$ cycloalkyl, $C_{1-6}$ alkoxy, $C_{3-6}$ cycloalkoxy, $NO_2$, $N(R^7)_2$, NH—C(O)—$R^7$; or NH—C(O)—NH—$R^7$, wherein each $R^7$ is independently: H, $C_{1-6}$ alkyl or $C_{3-6}$ cycloalkyl;

or $R^6$ is NH—C(O)—OR$^8$ wherein $R^8$ is $C_{1-6}$ alkyl or $C_{3-6}$ cycloalkyl;

$R^3$ is hydroxy, NH$_2$, or a group of formula —NH—$R^9$, wherein $R^9$ is $C_6$ or $C_{10}$ aryl, heteroaryl, —C(O)—$R^{10}$, —C(O)—NHR$^{10}$ or —C(O)—OR$^{10}$, wherein $R^{10}$ is $C_{1-6}$ alkyl or $C_{3-6}$ cycloalkyl;

D is a 3 to 7-atom saturated alkylene chain;

$R^4$ is H, or from one to three substituents at any carbon atom of said chain D, said substituent independently selected from: $C_{1-6}$ alkyl, $C_{1-6}$ haloalkyl, $C_{1-6}$ alkoxy, hydroxy, halo, amino, oxo, thio, and $C_{1-6}$ thioalkyl; and A is an amide of formula —C(O)—NH—$R^{11}$, wherein $R^{11}$ is selected from: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a carboxylic acid or a pharmaceutically acceptable salt or ester thereof;

said process comprising the following steps:

(i) reacting a compound of the formula (II) with a compound of the formula (III) to obtain a compound of the formula (IV):

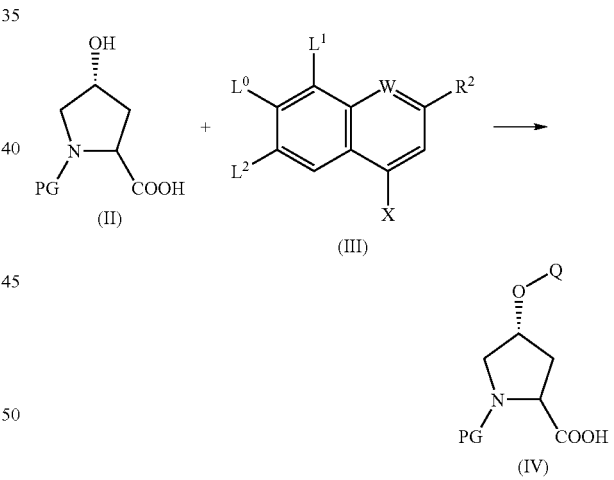

wherein PG is an amino protecting group, X is a halogen atom and Q is a substituent of the following formula:

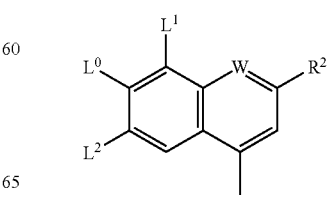

(ii) reacting a compound of the formula (IV) with a compound of the formula (V) to obtain a compound of the formula (VI):

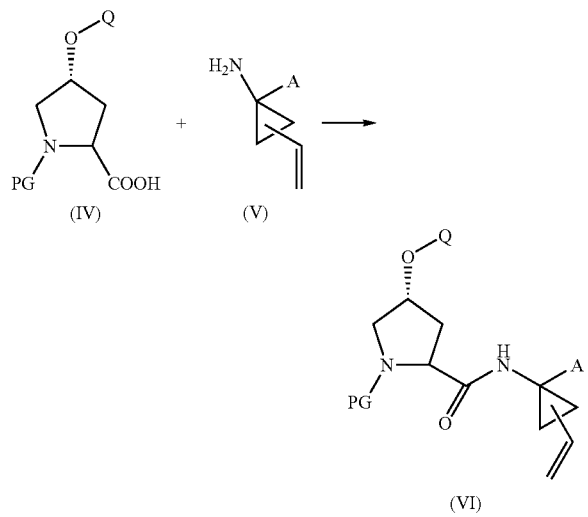

wherein A is an amide of formula —C(O)—NH—R$^{11}$, wherein R$^{11}$ is selected from the group consisting of: C$_{1-8}$ alkyl, C$_{3-6}$ cycloalkyl, C$_6$ or C$_{10}$ aryl; C$_{7-16}$ aralkyl and SO$_2$R$^{114}$ wherein R$^{114}$ is C$_{1-8}$ alkyl, C$_{3-7}$ cycloalkyl or C$_{1-6}$ alkyl-C$_{3-7}$ cycloalkyl;

or A is a protected carboxylic acid group;

(iii) removing the nitrogen protecting group in the compound of formula (VI) to obtain a compound of the formula (VII):

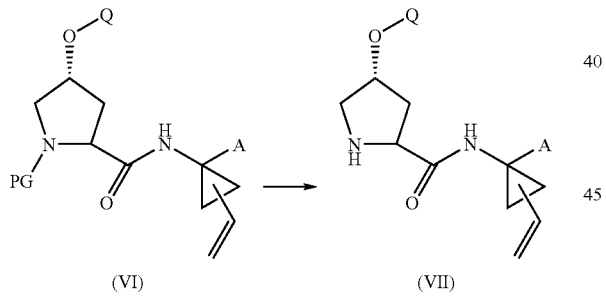

(iv) reacting a compound of the formula (VII) with a compound of the formula (VIII) to obtain a compound of the formula (IX):

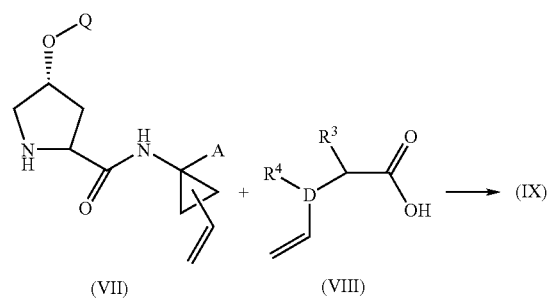

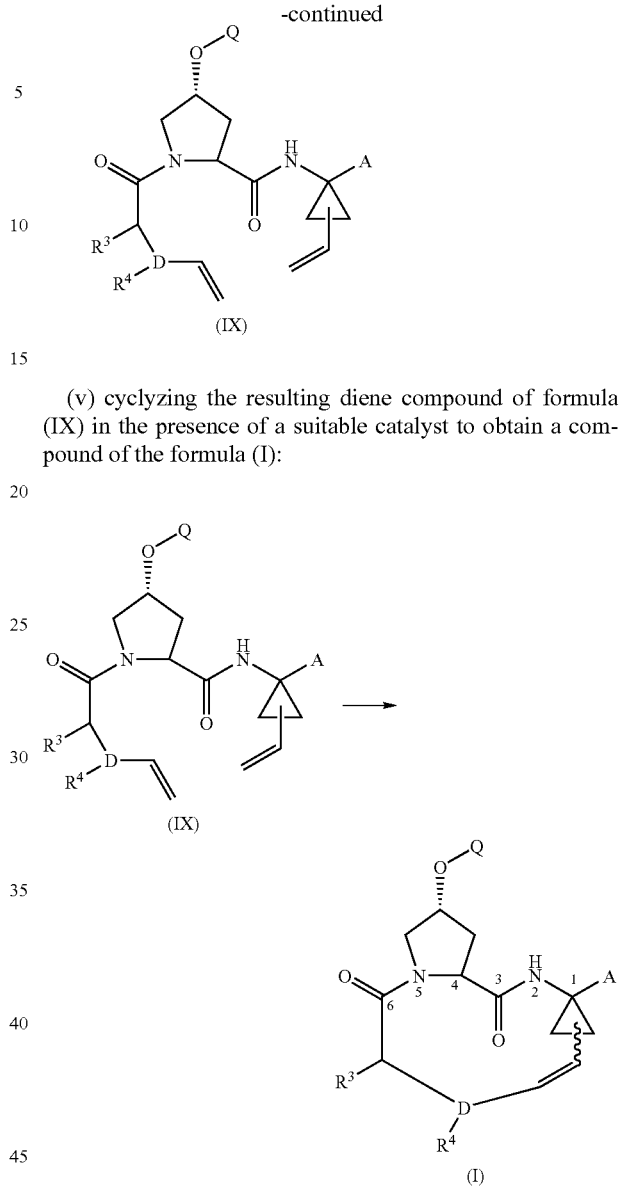

(v) cyclyzing the resulting diene compound of formula (IX) in the presence of a suitable catalyst to obtain a compound of the formula (I):

and when A is a protected carboxylic acid group, optionally subjecting the compound of formula (I) to deprotection (e.g., hydrolysis) conditions to obtain a compound of formula (I) wherein A is a carboxylic acid group;

and when A is a carboxylic acid group in the resulting compound of formula (I), optionally coupling this compound with a sulfonamide of formula R$^{114}$SO$_2$NH$_2$ in the presence of a suitable coupling agent, such as TBTU or HATU, to obtain a compound of formula (I) wherein A is —C(O)—NH—SO$_2$R$^{114}$.

II. The Individual Steps of the Synthetic Method

Additional embodiments of the invention are directed to the individual steps of the multistep general synthetic method described above and the individual intermediates used in these steps. These individual steps and intermediates of the present invention are described in detail below. All substituent groups are as defined in the general multi-step method above.

Step (i)

This step is directed to a process for preparing a compound of formula (IV), said process comprising reacting a compound of the formula (II) with a compound of the formula (III):

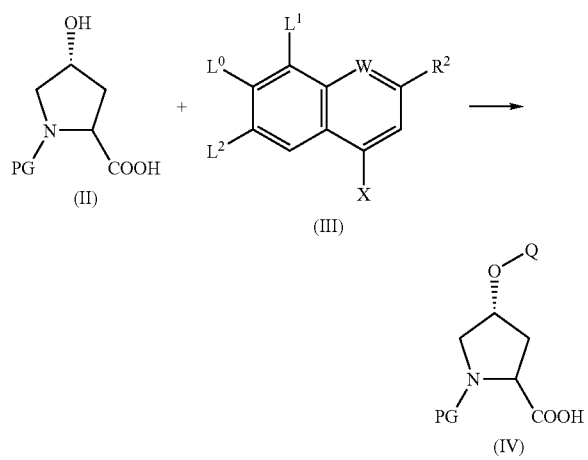

The coupling reaction between the compounds of formulas (II) and (III) is typically preformed in the presence of a base in a suitable solvent. Examples of suitable bases for this reaction include t-BuOK, t-BuONa, sodium bis(trimethylsilyl)amide, KDMO, with t-BuOK being a preferred base. Examples of suitable solvents for this reaction include polar aprotic solvents, for example, DMSO, DMF, NMP or other common polar aprotic solvents.

The amino-protecting group PG can be any suitable amino-protecting group that is well known in the art. See, e.g. those described in WO 00/09543, WO 00/09558. Typical examples of protecting groups that may be used are carbamate protecting groups such as Boc, or CBZ groups.

The X group in formula (III) is any halogen atom, but preferred is chlorine.

The compounds of formula (II) used as starting material are either commercially available, e.g., Boc-4(R)-hydroxyproline, or can be prepared from known materials using conventional techniques. In one example, the compounds of formula (II) may be prepared by amino-protection of the 4-hydroxyproline compounds of formula (X):

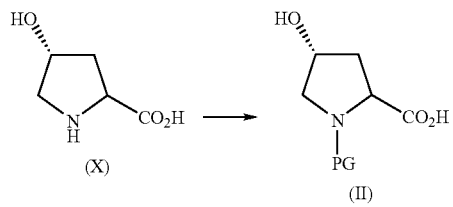

In the first step, an appropriate amino-protecting group is introduced onto the ring nitrogen atom of the 4-hydroxyproline compound of formula (X) using conventional procedures. For example, the compound of formula (X) may be dissolved in a suitable solvent and reacted with an appropriate amino-protecting group introducing reagent. For example, and not intending to be limited in its scope, when Boc (tert-butyloxycarbonyl) is the desired protecting group, compound (X) is reacted with the anhydride $Boc_2O$ (or Boc-ON) in a solvent mixture such as Acetone/Water, MIBK/Water or THF/Water to which a base such as NaOH, KOH, LiOH, triethylamine, diisopropylethylamine, or N-methyl-pyrrolidine is added, the reaction being carried out at a temperature between 20-60° C.

The halogen-substituted quinoline compounds of formula (III) can be prepared from the corresponding hydroxyl-substituted quinoline compounds of the following formula (III') by following well known halogenation procedures using various halogenation reagents under a variety of conditions known in the art. Examples of such reagents include the commonly used $POX_3$ and $PX_5$, where X=F, Cl, Br or I, wherein these reagents can be used in some cases as solvents or in combination with polar aprotic solvents, such as DMF or Acetonitrile.

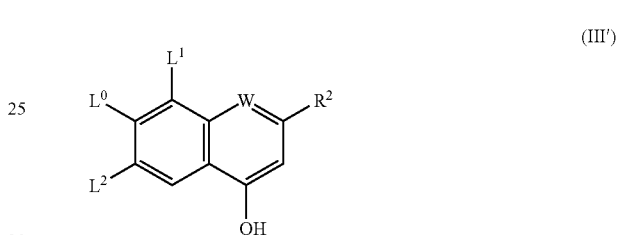

For examples of halogenation conditions that may be employed, see:

Chlorination: Outt, P. E. et al, *J Org Chem* 1998, 63 (17), 5762-5768 and references therein;

Bromination: Nakahara, S. et al, *Tetrahedron Lett* 1998, 39 (31), 5521-5522 and references therein Additional solvent: Nomoto, Y.; et al, *Chem Pharm Bull* 1990, 38 (8), 2179-2183.

The hydroxyl-substituted quinoline compounds of formula (III') can be synthesized from commercially available materials using the techniques described in WO 00/59929, WO 00/09543 and WO 00/09558, U.S. Pat. No. 6,323,180 B1, U.S. Pat. No. 6,608,027 B1 and U.S. Patent Application Publication No. 2005/0020503 A1.

Step (ii)

Step (ii) is directed to a process for preparing a compound of formula (VI) said process comprising reacting a compound of the formula (IV) with a compound of the formula (V):

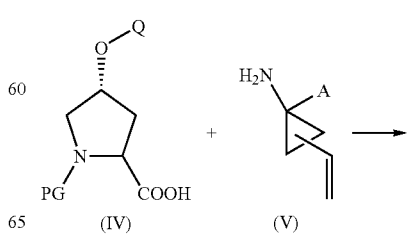

-continued

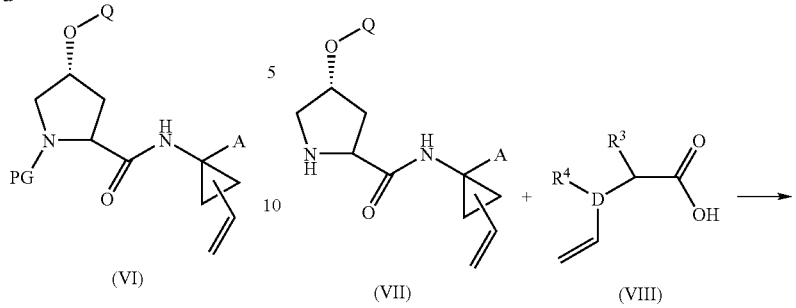

wherein A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl-$C_{3-7}$ cycloalkyl;

or A is a protected carboxylic acid group;

In this step, the compounds of formulas (IV) and (V) may be linked together by well known peptide coupling techniques. See, for example, the techniques disclosed in WO 00/09543, WO 00/09558 and U.S. Pat. No. 6,608,027 B1. Peptide coupling between compounds of formula (IV) and (V) could be obtained, for example, under a variety of conditions known in the art using conventional peptide coupling reagents such as DCC, EDC, TBTU, HBTU, HATU, DMTMM, HOBT, or HOAT in aprotic solvents such as dichloromethane, chloroform, THF, DMF, NMP, DMSO.

The compounds of formula (V) are known from WO 00/09543, WO 00/09558 and U.S. Pat. No. 6,608,027 B1, and may be prepared by techniques as described therein.

Step (iii)

Step (iii) is directed to a process for removing the nitrogen protecting group in the compound of formula (VI) to obtain a compound of the formula (VII):

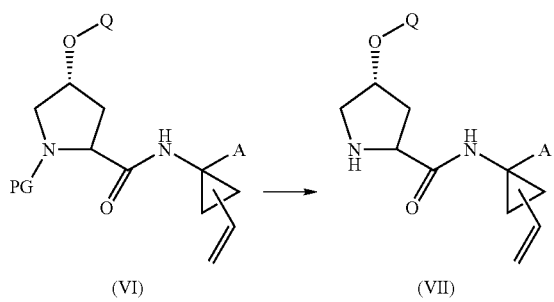

This step of cleaving the nitrogen protecting group in the compound of formula (VI) can also be accomplished by well known techniques, e.g., as described in 00/09543, WO 00/09558 and U.S. Pat. No. 6,608,027 B1. In particular embodiments, this process involves the acid hydrolysis of the compound of formula (VI) with an organic or inorganic acid, such as HCl, $H_2SO_4$, TFA, AcOH, $MeSO_3H$, in a variety of protic or polar nonprotic solvents such as alcohols, ethers, ACN or DCM.

Step (iv)

Step (iv) is directed to a process for preparing a compound of formula (IX) said process comprising reacting a compound of the formula (VII) with a compound of the formula (VIII):

In this step, the compounds of formulas (VII) and (VIII) may be linked together by the same well known peptide coupling techniques as described above in step (ii) for the peptide coupling of formulas (IV) and (V). Examplary conditions are the same as described above for step (ii).

The substituted acid compound of formula (VIII) used as a starting material are known from U.S. Pat. No. 6,608,027 B1 and may be obtained from commercially available materials using the techniques as described therein.

Step (v)

Step (v) is directed to a process for preparing a compound of the formula (I) said process comprising cyclyzing the resulting diene compound of formula (IX) in the presence of a suitable catalyst to obtain a compound of the formula (I):

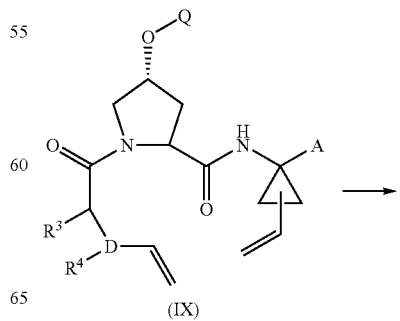

-continued

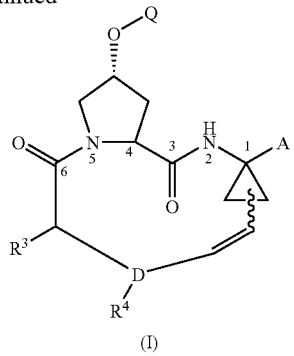

(I)

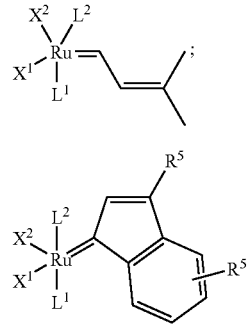

(D)

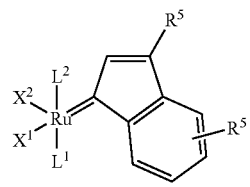

(E)

and when A is a protected carboxylic acid group, optionally subjecting the compound of formula (I) to deprotection (e.g., hydrolysis) conditions to obtain a compound of formula (I) wherein A is a carboxylic acid group;

and when A is a carboxylic acid group in the resulting compound of formula (I), optionally coupling this compound with a sulfonamide of formula $R^{114}SO_2NH_2$ in the presence of a suitable coupling agent, such as TBTU or HATU, to obtain a compound of formula (I) wherein A is —C(O)—NH—SO_2R^{114}.

Suitable ring-closing catalysts for this step include ruthenium based catalysts. For example, any of the well-known ruthenium based catalysts used in olefin metathesis reactions, such as Grubb's catalyst (first and second generation), Hoveyda's catalyst (first and second generation) and Nolan's catalyst, may be used with appropriate adjustment of reaction conditions as may be necessary to allow ring-closing to proceed, depending upon the particular catalyst this is selected.

Suitable ruthenium catalysts for the cyclization step include, for example, the compounds of formula A, B, C, D or E:

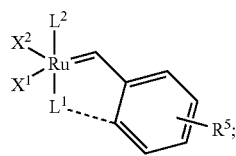
(A)

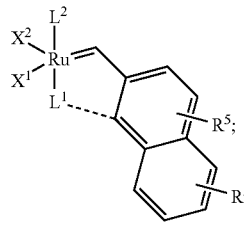
(B)

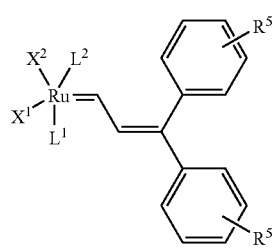
(C)

wherein $X^1$ and $X^2$ each independently represent an anionic ligand, $L^1$ represents a neutral electron donor ligand which is bonded to the ruthenium atom and is optionally bonded to the phenyl group, and $L^2$ represents a neutral electron donor ligand which is bonded to the ruthenium atom;

and $R^5$ is selected from one or more substituents on the benzene ring, each substituent independently selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl; and wherein $X^2$ and $L^2$ may optionally together form a chelating bidentate ligand.

In a more specific embodiment, the ruthenium catalyst is a compound of formula (A-1) or (A-2):

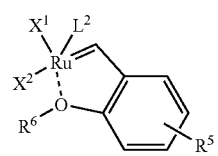
(A-1)

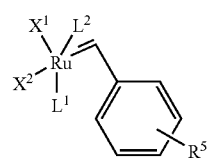
(A-2)

wherein:

$L^1$ is a trisubstituted phosphine group of the formula PR_3, wherein R is selected from $C_{1-6}$alkyl and $C_{3-8}$cycloalkyl, $L^2$ is a trisubstituted phosphine group of the formula PR_3, wherein R is selected from $C_{1-6}$alkyl and $C_{3-8}$cycloalkyl, or $L^2$ is a group of the formula A or B:

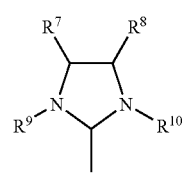
(A)

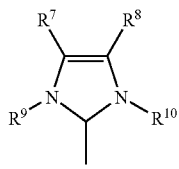

(B)

wherein $R^7$ and $R^8$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group; and $R^9$ and $R^{10}$ each independently represent a hydrogen atom or a $C_{1-6}$ alkyl, $C_{2-6}$ alkenyl, $C_{6-12}$ aryl or $C_{6-12}$ aryl-$C_{1-6}$ alkyl group, each optionally substituted by one, two or three groups selected from hydrogen, $C_{1-6}$alkyl, halo$C_{1-6}$alkyl, HS—$C_{1-6}$alkyl, HO—$C_{1-6}$alkyl, perfluoro$C_{1-6}$alkyl, $C_{3-6}$ cycloalkyl, $C_{1-6}$alkoxy, hydroxyl, halogen, nitro, imino, oxo, thio or aryl;

$X^1$ and $X^2$ each independently represent a halogen atom;

$R^5$ represent hydrogen or nitro; and $R^6$ represents a $C_{1-6}$ alkyl group.

In another more specific embodiment, the ruthenium catalyst is selected from:

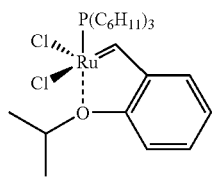

1st generation Hoveyda's Catalyst

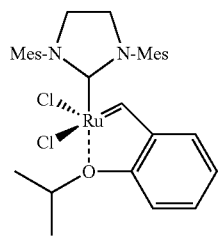

2st generation Hoveyda's Catalyst

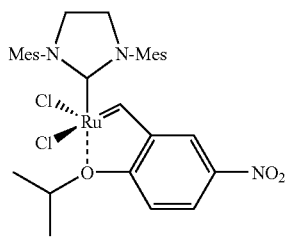

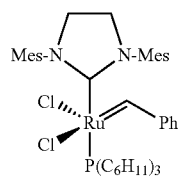

1st generation Grubb's Catalyst    2nd generation Grubb's Catalyst

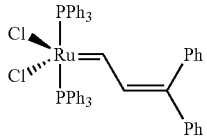

where Ph is phenyl and Mes is 2,4,6-trimethylphenyl.

Ruthenium-based catalysts useful for the metathesis cyclization step, such as those set forth above, are all known catalysts that may be obtained by known synthetic techniques. For example, see the following references for examples of suitable ruthenium-based catalysts:

Organometallics 2002, 21, 671; 1999, 18, 5416; and 1998, 17, 2758;

J. Am. Chem. Soc. 2001, 123, 6543; 1999, 121, 791; 1999, 121, 2674; 2002, 124, 4954; 1998, 120, 2484; 1997, 119, 3887; 1996, 118, 100; and 1996, 118, 9606

J. Org. Chem. 1998, 63, 9904; and 1999, 64, 7202;

Angew. Chem. Int. Ed. Engl. 1998, 37, 2685; 1995, 34, 2038; 2000, 39, 3012 and 2002, 41, 4038;

U.S. Pat. Nos. 5,811,515; 6,306,987 B1; and 6,608,027 B1

In another specific embodiment of the present invention the ring-closing reaction of step (v) is carried out in the presence of a diluent in a temperature range from about 30° to about 120° C., preferably from about 90° to about 108° C., in particular at about 100° C.

In another specific embodiment of the present invention the ring-closing reaction of step (v) is carried out in the presence of a diluent selected from alkanes, such as n-pentane, n-hexane or n-heptane, aromatic hydrocarbons, such as benzene, toluene or xylene, chlorinated hydrocarbons such as dichloromethane, trichloromethane, tetrachloromethane or dichloroethane, ether solvents, such as tetrahydrofuran, 2-methyl-tetrahydrofuran, 3-methyl-tetrahydrofuran, cyclopentyl methyl ether, methyl tert-butyl ether, dimethyl ether, diethyl ether or dioxane and methyl alcohol.

In another specific embodiment of the present invention the ring-closing reaction of step (v) is carried out wherein the molar ratio of the diene compound of formula IX to the catalyst ranges from 1000:1 to 100:1, preferably from 500:1 to 110:1, in particular from 250:1 to 150:1.

In another specific embodiment of the present invention the ring-closing reaction of step (v) is carried out at a ratio of the diene compound of formula IX to diluent in the range from 1:400 by weight to 1:25 by weight, preferably from 1:200 by weight to 1:50 by weight, in particular from 1:150 by weight to 1:75 by weight.

In another specific embodiment of the present invention the ring-closing reaction of step (v) is carried out by portionwise addition of the catalyst in the range from 2 to 6 portions, preferably from 3-5 portions, in particular 4 portions.

One skilled in the art can readily optimize the cyclization step by selecting and adjusting appropriate conditions suitable for the particular ring-closing catalyst selected. For example, depending upon the catalyst selected it may be preferable to run the cyclization step at high temperature, e.g., higher than 90° C., although lower temperatures may also be possible with the addition of an activator such as copper halide (CuX, where X is halogen) to the reaction mixture.

In another specific embodiment, this ring-closing reaction of step (v) is performed using the 2nd generation Hoveyda's catalyst, in a temperature range of from about 90° to about 108° C., for example at about 100° C., in the presence of an aromatic hydrocarbon diluent, for example toluene, using portionwise addition of the catalyst in the range from 2 to 6 portions, for example from 3-5 portions, in particular 4 portions.

Alternatively, this ring-closing reaction of step (v) is performed using the 2$^{nd}$ generation Hoveyda's catalyst, in a temperature range of from about 30° to about 45° C., for example at about 40° C., in the presence of a suitable activator such as copper iodide, in a chlorinated hydrocarbon diluent or an aromatic hydrocarbon diluent, for example dichloromethane, using a one-pot addition or a portionwise addition of the catalyst in the range from 2 to 4 portions, in particular a one-pot addition.

In a particular embodiment of this step, the compound of formula (IX) is dissolved in a degassed organic solvent (such as toluene or dichloromethane) to a concentration below about 0.02M, then treated with a ruthenium-based catalyst such as Hoveyda's catalyst, at a temperature from about 40° C. to about 110° C. until completion of the reaction. Some or all of the ruthenium metal may be removed from the reaction mixture by treatment with a suitable heavy metal scavenger, such as THP or other agents known to scavenge heavy metals. The reaction mixture is washed with water, followed by partial concentration of the organic solution (e.g., by distillation process). The organic solution may be decolorized, such as by the addition of activated charcoal with subsequent filtration, and then is added to a suitable solvent at a suitable temperature, such as pre-cooled methylcyclohexane, which causes precipitation of the product compound of formula (I) that is collected by filtration.

When A is a carboxylic acid ester group in formula (I), the esterified compound of formula (I) can optionally be subjected to hydrolysis conditions to obtain the corresponding free carboxylic acid compound. Hydrolysis can be carried out using conventional hydrolysis conditions known in the art. In a particular embodiment, for example, the esterified compound of formula (I) is dissolved in an organic solvent such as THF, and a suitable hydrolyzing agent such as lithium hydroxide monohydrate (LiOH.H$_2$O) is added followed by the addition of water. The resultant solution is stirred at a temperature from about 35° C. to about 50° C. At the end of the reaction, the solution is cooled, and the organic layer collected. A suitable solvent such as ethanol is added to the organic layer and the pH is adjusted to from about pH 5 to about pH 6. The mixture is then warmed to a temperature from about 40° C. to about 50° C. at which point water is added and solution is stirred whereupon the compound of formula (I) begins to precipitate. Upon completion of the precipitation, the solution is cooled to ambient temperature and the compound of formula (I) is collected by filtration, washed and dried.

III. Preferred Embodiments of the Compound of Formula (I)

Preferred embodiments include compounds of formula (I) as described above, wherein the cyclopropyl moiety R$^B$ is selected from the 2 different diastereoisomers where the 1-carbon center of the cyclopropyl has the R configuration as represented by structures (i) and (ii):

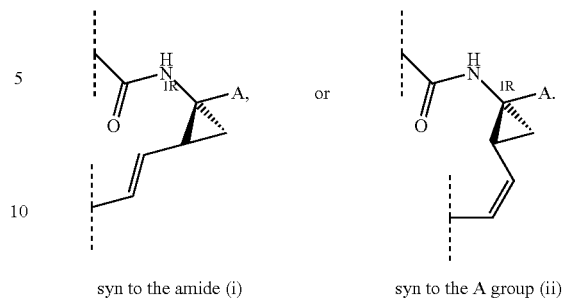

syn to the amide (i)     syn to the A group (ii)

In one specific embodiment of the compounds of formula (I), the olefin group is in the configuration syn to the A group as represented by structure (ii) above;

W is N;

L$^0$ is selected from H, —OH, —OCH$_3$, —OC$_2$H$_5$, —OC$_3$H$_7$, —OCH(CH$_3$)$_2$, —NHCH$_3$, —NHC$_2$H$_5$, —NHC$_3$H$_7$, —NHCH(CH$_3$)$_2$, —N(CH$_3$)$_2$, —N(CH$_3$)C$_2$H$_5$, —N(CH$_3$)C$_3$H$_7$ and —N(CH$_3$)CH(CH$_3$)$_2$.

L$^1$ and L$^2$ are each independently selected from hydrogen, fluorine, chlorine, bromine, —CH$_3$, —C$_2$H$_5$, —C$_3$H$_7$, —CH(CH$_3$)$_2$, —OCH$_3$, —OC$_2$H$_5$, —OC$_3$H$_7$ and —OCH(CH$_3$)$_2$, R$^2$ is H, C$_{1-6}$ thioalkyl, C$_{1-6}$ alkoxy, phenyl or Het selected from the following:

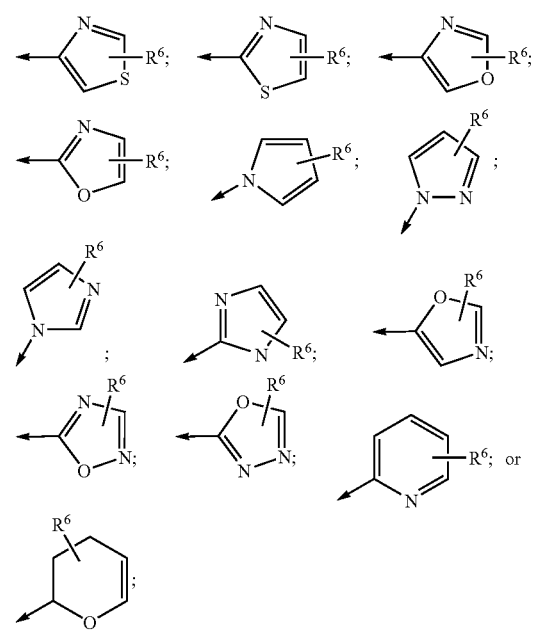

wherein R$^6$ is H, C$_{1-6}$ alkyl, NH—R$^7$, NH—C(O)—R$^7$, NH—C(O)—NH—R$^7$, wherein each R$^7$ is independently: H, C$_{1-6}$ alkyl, or C$_{3-6}$ cycloalkyl;

or R$^6$ is NH—C(O)—OR$^8$, wherein R$^8$ is C$_{1-6}$ alkyl;

R$^3$ is NH—C(O)—R$^{10}$, NH—C(O)—OR$^{10}$ or NH—C(O)—NR$^{10}$, wherein in each case R$^{10}$ is C$_{1-6}$ alkyl, or C$_{3-6}$ cycloalkyl; and D is a 4 to 6-atom saturated alkylene chain;

R$^4$ is H or C$_{1-6}$ alkyl;

and A is a carboxylic acid or a pharmaceutically acceptable salt or ester thereof.

In another specific embodiment of the compounds of formula (I), the olefin group is in the configuration syn to the A group as represented by structure (ii) above;

W is N;

L⁰ is selected from H, —OH, —OCH₃ and —N(CH₃)₂;

one of L¹ and L² is —CH₃, —F, —Cl or —Br and the other of L¹ and L² is H, or both L¹ and L² are H;

$R^2$ is

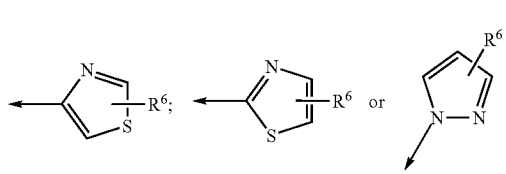

wherein $R^6$ is NH—$R^7$ or NH—C(O)—$R^7$, wherein $R^7$ is independently: $C_{1-6}$ alkyl, or $C_{3-6}$ cycloalkyl;

$R^3$ is NH—C(O)—$OR^{10}$, wherein $R^{10}$ is $C_{1-6}$ alkyl, or $C_{3-6}$ cycloalkyl;

$R^4$ is H or $C_{1-6}$ alkyl;

D is a 5-atom saturated alkylene chain; and

A is a carboxylic acid or a pharmaceutically acceptable salt or ester thereof.

In another specific embodiment of the compounds of formula (I), the olefin group is in the configuration syn to the A group as represented by structure (ii) above;

W is N;

L⁰ is —OCH₃;

L¹ is —CH₃, —F, —Cl or —Br and and L² is H, or both L¹ and L² are H;

$R^2$ is

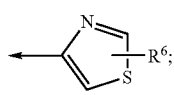

wherein $R^6$ is NH—$R^7$ or NH—C(O)—$R^7$, wherein $R^7$ is independently: $C_{1-6}$ alkyl or $C_{3-6}$ cycloalkyl;

$R^3$ is NH—C(O)—$OR^{10}$, wherein $R^{10}$ is butyl, cyclobutyl or cyclopentyl;

$R^4$ is H or $C_{1-3}$ alkyl;

D is a 5-atom saturated alkylene chain; and

A is a carboxylic acid or a pharmaceutically acceptable salt or ester thereof.

The following table lists compounds representative of the compounds of formula (I). A compound of the formula below:

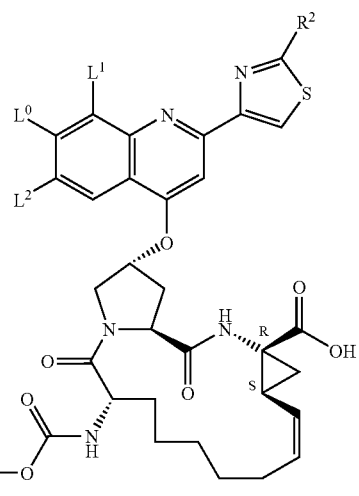

wherein L⁰, L¹, L² and $R^2$ are as defined below:

| Cpd # | L² | L⁰ | L¹ | R² |
|---|---|---|---|---|
| 101 | H | —OMe | Me | |
| 102 | H | —OMe | Me | |
| 103 | H | —OMe | Me | |
| 104 | H | —OMe | Me | |
| 105 | H | —OMe | Br | |
| 106 | H | —OMe | Br | |
| 107 | H | —OMe | Cl | |
| 108 | H | —OMe | Cl | |

-continued

| Cpd # | L² | L⁰ | L¹ | R² |
|---|---|---|---|---|
| 109 | Me | —OMe | Me | -NH-iPr |
| 110 | Me | —OMe | Me | -NH-C(O)-Et |
| 111 | H | —OMe | F | -NH-iPr |
| 112 | H | —OMe | F | -NH-C(O)-Et |
| 113 | H | —OMe | Cl | -NH-C(O)-Pr |
| 114 | H | —OMe | Br | -NH-C(O)-Pr |
| 115 | H | —OMe | Br | -NH-C(O)-iPr |

-continued

| Cpd # | L² | L⁰ | L¹ | R² |
|---|---|---|---|---|
| 116 | H | —OMe | Br | -NH-C(O)-O-iPr |

The following table list additional compounds representative of the compounds of formula (I). A compound of the formula below:

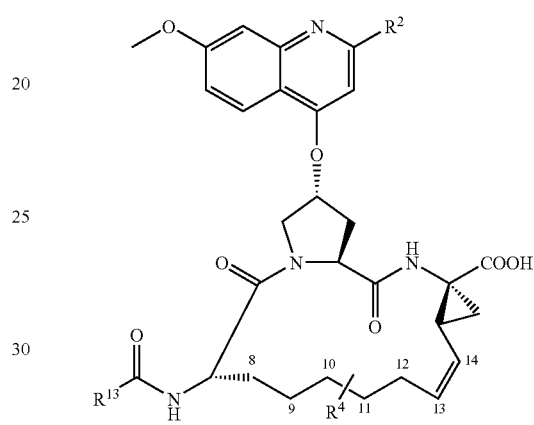

wherein the bond from position 14 to the cyclopropyl group is syn to the COOH, said 13, 14 double bond is cis, $R^{13}$, $R^4$ and $R^2$ are defined as follows:

| Cpd # | R¹³: | R⁴: | R²: |
|---|---|---|---|
| 201 | cyclobutyl-O- | H | thiazol-2-yl-NH-C(O)-CH₃ |
| 202 | t-Bu-CH(Me)-NH- | H | thiazol-2-yl-NH-C(O)-CH₃ |
| 203 | cyclopentyl-O- | H | pyrrol-1-yl |
| 204 | cyclopentyl-O- | H | OEt; |
| 205 | iPr-O- | H | OEt; |

-continued
| Cpd # | R¹³: | R⁴: | R²: |
|---|---|---|---|
| 206 | 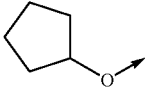 | H | 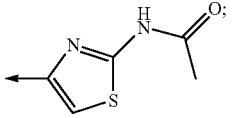 |
| 207 | 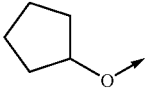 | H | 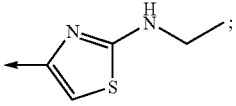 |
| 208 | 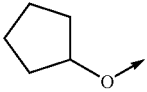 | H | 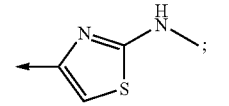 |
| 209 | 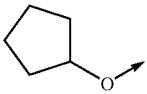 | H | 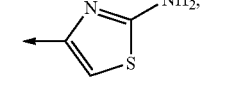 |
| 210 | 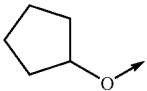 | H | 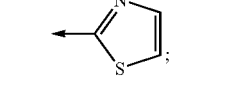 |
| 211 | 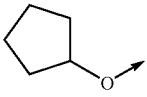 | H | 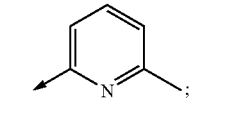 |
| 212 | 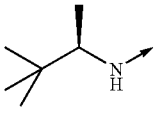 | H | 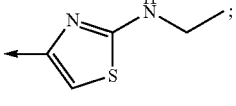 |
| 213 | 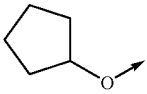 | H | 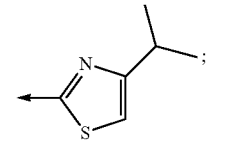 |
| 214 | 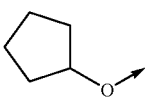 | H | 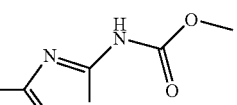 |
| 215 | 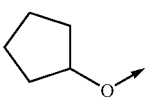 | H | 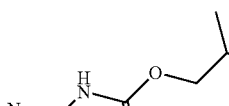 |

-continued

| Cpd # | R¹³: | R⁴: | R²: |
|---|---|---|---|
| 216 | cyclobutyl-O- | H | 4-thiazolyl-NH-ethyl |
| 217 | cyclopentyl-O- | H | pyrazol-1-yl |
| 218 | cyclopentyl-O- | H | 4-thiazolyl-NH-isopropyl |
| 219 | cyclopentyl-O- | H | pyrazol-1-yl (3-position linked) |
| 220 | cyclopentyl-O- | 10-(R) Me | OEt |
| 221 | cyclopentyl-O- | H | 4-thiazolyl-NH-cyclopropyl |
| 222 | cyclopentyl-O- | H | 4-thiazolyl-NH-cyclobutyl |
| 223 | cyclopentyl-O- | H | 4-thiazolyl-NH-cyclopentyl |
| and 224 | cyclopentyl-O- | H | 4-thiazolyl-NH-cyclohexyl |

We claim:

1. A process for preparing a compound of the following formula (I), or a pharmaceutically acceptable salt or ester thereof:

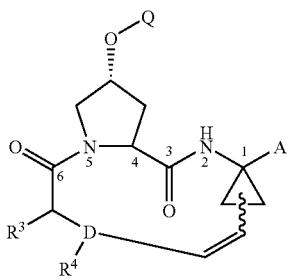

(I)

wherein Q is a substituent of the following formula:

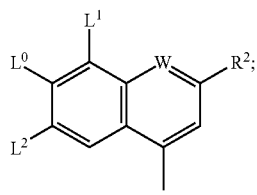

the olefin group attached to the cyclopropyl ring is in the configuration syn to the A group as represented by the following structure:

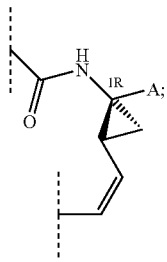

W is N;
$L^0$ is selected from H, —OH, —OCH$_3$ and —N(CH$_3$)$_2$;
one of $L^1$ and $L^2$ is —CH$_3$, —F, —Cl or —Br and the other of $L^1$ and $L^2$ is H, or both $L^1$ and $L^2$ are H;
$R^2$ is

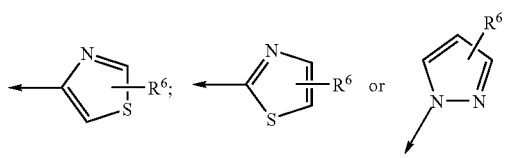

wherein $R^6$ is NH—$R^7$ or NH—C(O)—$R^7$, wherein $R^7$ is independently: $C_{1-6}$ alkyl, or $C_{3-6}$ cycloalkyl;

$R^3$ is NH—C(O)—O$R^{10}$, wherein $R^{10}$ is $C_{1-6}$ alkyl, or $C_{3-6}$ cycloalkyl;
$R^4$ is H or $C_{1-6}$ alkyl;
D is a 5-atom saturated alkylene chain; and
A is a carboxyl group, said process comprising the step of cyclyzing a diene compound of formula (IX) in the presence of a suitable catalyst to obtain a compound of the formula (I):

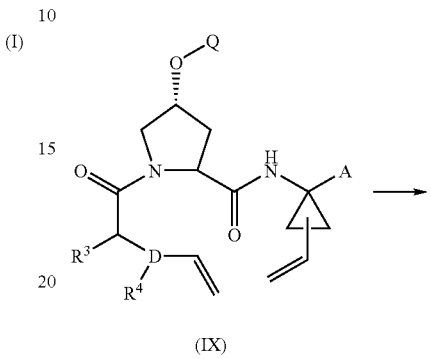

(IX)

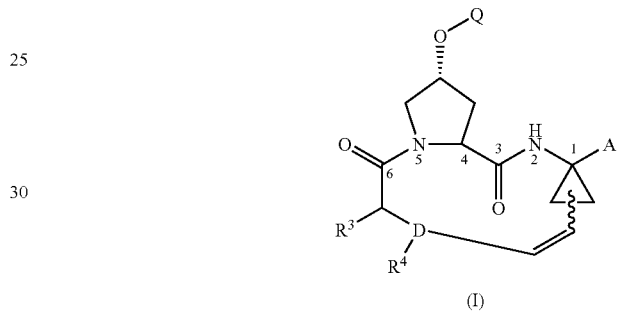

(I)

and when A is a protected carboxylic acid group, optionally subjecting the compound of formula (I) to deprotection (e.g., hydrolysis) conditions to obtain a compound of formula (I) wherein A is a carboxylic acid group;
and when A is a carboxyl group in the resulting compound of formula (I), optionally coupling this compound with a sulfonamide of formula $R^{114}SO_2NH_2$, in which $R^{114}$ is $C_{1-8}$-alkyl, $C_{3-7}$-cycloalkyl or $C_{1-6}$-alkyl-$C_{3-7}$-cycloalkyl, in the presence of a suitable coupling agent to obtain a compound of formula (I) wherein A is -C(O)—NH—SO$_2$R$^{114}$.

2. A process according to claim 1, wherein the catalyst is a ruthenium based catalyst.

3. A process according to claim 1, wherein the reaction is carried out in the presence of a diluent in a temperature range from about 30° to about 120 °C.

4. A process according to claim 3, wherein the diluent is selected from alkanes, aromatic hydrocarbons, chlorinated hydrocarbons, ether solvents and methyl alcohol.

5. A process according to claim 1, wherein the catalyst is the 2$^{nd}$ generation Hoveyda's catalyst, and the reaction is carried out at a temperature in the range of from about 90° to about 108 °C., in the presence of an aromatic hydrocarbon diluent, and using portionwise addition of the catalyst in the range of from 2 to 6 portions.

6. A process according to claim 1, wherein the catalyst is the 2$^{nd}$ generation Hoveyda's catalyst, and the reaction is carried out at a temperature in the range of from about 30° to about 45° C., in the presence of a suitable activator, in a chlorinated hydrocarbon diluent or an aromatic hydrocarbon diluent, using a one-pot addition of catalyst or a portionwise addition of the catalyst in the range from 2 to 4 portions.

7. A process according to claim 1, wherein the diene compound (IX) is prepared by a process comprising the following steps:

(i) reacting a compound of the formula (II) with a compound of the formula (III) to obtain a compound of the formula (IV):

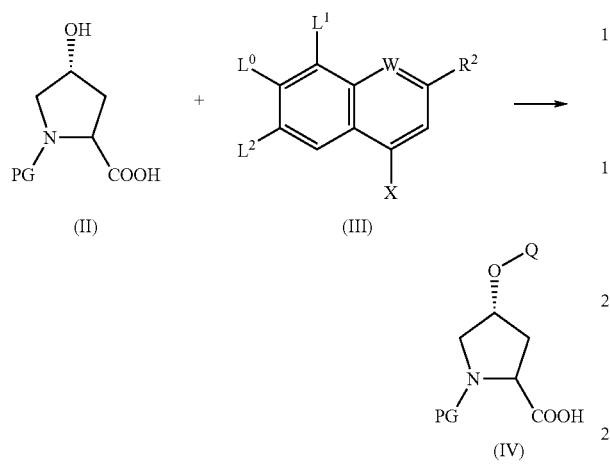

wherein PG is an amino protecting group, X is a halogen atom and Q is a substituent of the following formula:

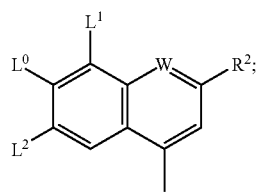

(ii) reacting a compound of the formula (IV) with a compound of the formula (V) to obtain a compound of the formula (VI):

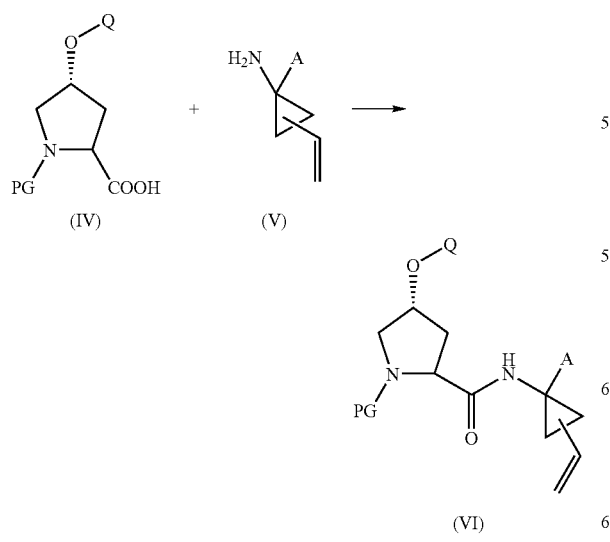

wherein A is an amide of formula —C(O)—NH—$R^{11}$, wherein $R^{11}$ is selected from the group consisting of: $C_{1-8}$ alkyl, $C_{3-6}$ cycloalkyl, $C_6$ or $C_{10}$ aryl; $C_{7-16}$ aralkyl and $SO_2R^{11A}$ wherein $R^{11A}$ is $C_{1-8}$ alkyl, $C_{3-7}$ cycloalkyl or $C_{1-6}$ alkyl—$C_{3-7}$ cycloalkyl;

or A is a protected carboxylic acid group;

(iii) removing the nitrogen protecting group in the compound of formula (VI) to obtain a compound of the formula (VII):

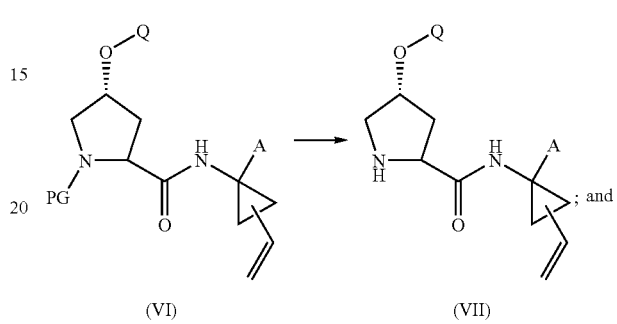

(iv) reacting a compound of the formula (VII) with a compound of the formula (VIII) to obtain a compound of the formula (IX):

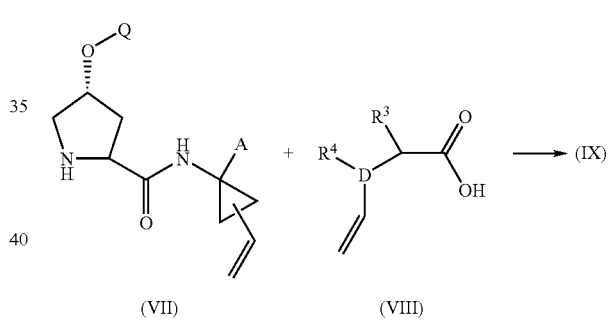

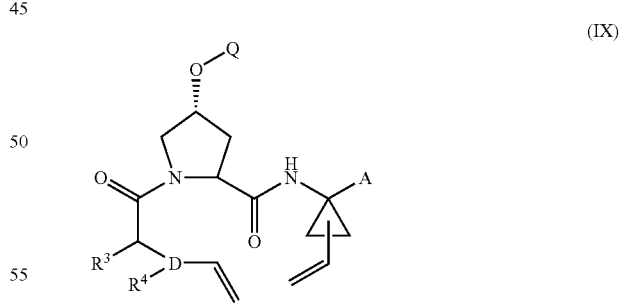

wherein W, $L^0$, $L^1$, $L^2$, $R^2$, $R^3$, $R^4$, D, and A in each of the above steps are as defined in claim 1.

8. A process according to claim 1, wherein:
W is N;
$L^0$ is —$OCH_3$;
$L^1$ is —$CH_3$, —F, —Cl or —Br and $L^2$ is H, or both $L^1$ and $L^2$ are H;

$R^2$ is

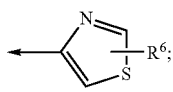

wherein $R^6$ is NH—$R^7$ or NH—C(O)—$R^7$, wherein $R^7$ is independently:
$C_{1-6}$ alkyl or $C_{3-6}$ cycloalkyl;
$R^3$ is NH—C(O)$R^{10}$, wherein $R^{10}$ is butyl, cyclobutyl or cyclopentyl;
$R^4$ is H or $C_{1-3}$alkyl;
D is a 5-atom saturated alkylene chain; and
A is a carboxyl group.

9. A compound of the following formula (IV):

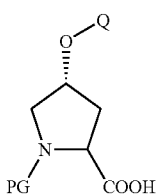

(IV)

wherein PG is an amino protecting group and Q is a substituent of the following formula:

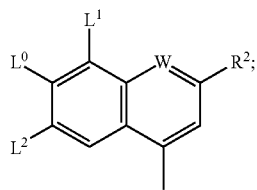

wherein:
W is N;
$L^O$ is selected from H, —OH, —$OCH_3$ and —$N(CH_3)_2$;
one of $L^1$ and $L^2$ is —$CH_3$, —F, —Cl or —Br and the other of $L^1$ and $L^2$ is H, or both $L^1$ and $L^2$ are H; and
$R^2$ is

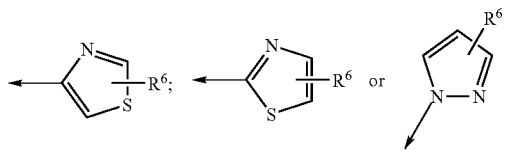

wherein $R^6$ NH—$R^7$ NH—C(O)—
$R^7$, wherein $R^7$ is independently: $C_{1-6}$ alkyl, or $C_{3-6}$ cycloalkyl.

10. A compound of formula (IV) according to claim 9, wherein:
W is N;
$L^0$ is —$OCH_3$;
$L^1$ is —$CH_3$, —F, —Cl or —Br and $L^2$ is H, or both $L^1$ and $L^2$ are H; and $R^2$ is

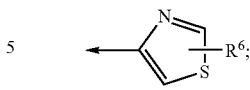

wherein $R^6$ is NH—$R^7$ or NH—C(O)—$R^7$, wherein $R^7$ is independently:
$C_{1-6}$ alkyl or $C_{3-6}$ cycloalkyl.

11. A process for preparing a compound of formula (IV) according to claim 9, said process comprising the step of reacting a compound of the formula (II) with a compound of the formula (III) to obtain a compound of the formula (IV):

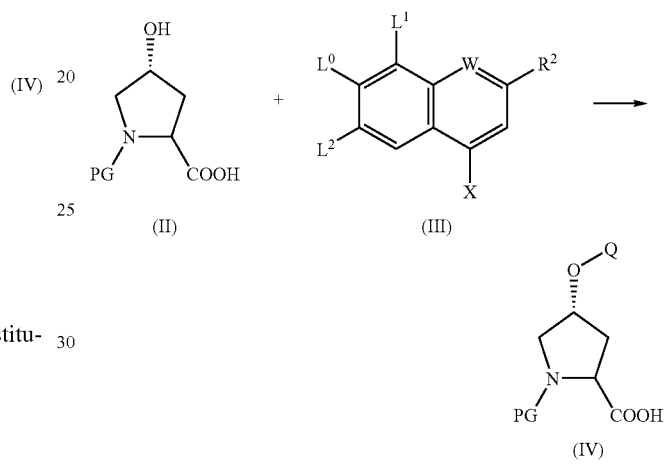

wherein PG is an amino protecting group, X is a halogen atom and Q is a substituent of the following formula:

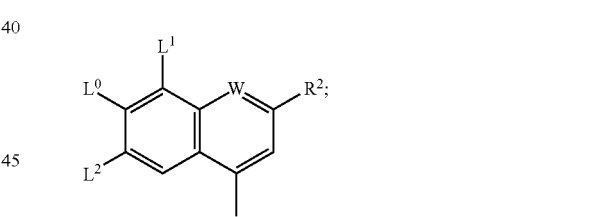

wherein W, $L^O$, $L^1$, $L^2$, and $R^2$ are as defined in claim 9.

12. A compound of the following formula (IX), or a pharmaceutically acceptable salt or ester thereof:

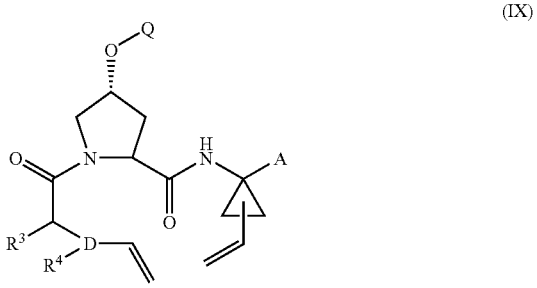

(IX)

wherein Q is a substituent of the following formula:

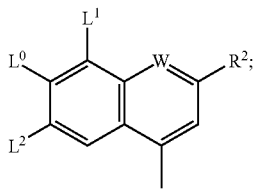

the olefin group attached to the cyclopropyl ring is in the configuration syn to the A group as represented by the following structure:

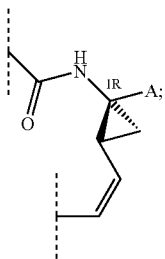

W is N;
$L^O$ selected from H, —OH, —OCH$_3$ and —N(CH$_3$)$_2$;
one of $L^1$ and $L^2$ is —CH$_3$, —F, —Cl or —Br and the other of $L^1$ and $L^2$ H, or both $L^1$ and $L^2$ are H;
$R^2$ is

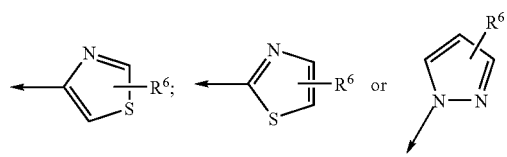

wherein $R^6$ is NH—$R^7$ or NH—C(O)—
$R^7$, wherein $R^7$ is independently: C$_{1-6}$ alkyl, or C$_{3-6}$ cycloalkyl;
$R^3$ is NH—C(O)—OR$^{10}$, wherein R$^{10}$ is C$_{1-6}$ alkyl, or C$_{3-6}$ cycloalkyl;
$R^4$ is H or C$_{1-6}$alkyl;
D is a 5-atom saturated alkylene chain; and
A is a carboxyl group.

13. A compound of formula (IX) according to claim 12, wherein:
W is N;
$L^O$ is —OCH$_3$;
$L^1$ is —CH$_3$, —F, —Cl or —Br and $L^2$ H, or both $L^1$ and $L^2$ are H;
$R^2$ is

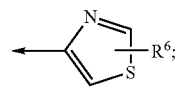

wherein $R^6$ is NH—R or NH—C(O)—$R^7$, wherein $R^7$ is independently:
C$_{1-6}$alkyl or C$_{3-6}$ cycloalkyl;
$R^3$ is NH—C(O)OR$^{10}$, wherein R$^{10}$ is butyl, cyclobutyl or cyclopentyl;
$R^4$ is H or C$_{1-3}$ alkyl;
D is a 5-atom saturated alkylene chain; and
A is a carboxyl group.

* * * * *